(12) United States Patent
Chwalsz et al.

(10) Patent No.: US 6,451,780 B1
(45) Date of Patent: Sep. 17, 2002

(54) PROGESTERONE ANTAGONISTS FOR THE PRODUCTION OF PHARMACEUTICAL AGENTS FOR THE TREATMENT OF DYSFUNCTIONAL UTERINE BLEEDING

(75) Inventors: Kristof Chwalsz; Klaus Stöckemann, both of Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/615,060

(22) Filed: Jul. 12, 2000

Related U.S. Application Data

(63) Continuation of application No. 09/159,474, filed on Sep. 23, 1998, now abandoned, which is a continuation of application No. 08/718,500, filed as application No. PCT/EP95/00394 on Feb. 2, 1995, now abandoned.

(51) Int. Cl.[7] ............................................... A61K 31/56
(52) U.S. Cl. ....................................... 514/179; 514/899
(58) Field of Search .......................................... 514/179

(56) References Cited

U.S. PATENT DOCUMENTS 5,622,943 A    4/1997    Hodgen ....................... 514/179

OTHER PUBLICATIONS

WPIDS 88–159461; RD 289076 A 880510 (8823).
WPIDS 94–007063; Hodgen, G.D.; WO 9321927 A1 931111.
Biosis 90:496750; Coutinho, E.M.; Gynecol Obstet invest 30 (1), 1990, 44–47.
Embase 88154852; Ulman et al.; Horm. Res., (1987) 28/2–4 (274–278).
Biosis 87:46804; Cutinho, E. M.; Am J Obstet Gynecol 155 (4), 1986, 761–767.

*Primary Examiner*—Rebecca Cook
(74) *Attorney, Agent, or Firm*—Millen, White, Zelano & Branigan, P.C.

(57) ABSTRACT

Competitive progesterone antagonists (antigestagens) are suitable for the production of pharmaceutical agents for the treatment of forms of dysfunctional uterine bleeding (metrorrhagias, menorrhagias, hypermenorrhea).

11 Claims, No Drawings

PROGESTERONE ANTAGONISTS FOR THE PRODUCTION OF PHARMACEUTICAL AGENTS FOR THE TREATMENT OF DYSFUNCTIONAL UTERINE BLEEDING

This is a continuation, of application Ser. No. 09/159,474 filed Sep. 23, 1998 abandoned; which is a continuation of application Ser. No. 08/718,500 filed Oct. 1, 1996 (now abandoned) which is a 317 of PCT/EP 95/00394 filed Feb. 2, 1995.

BACKGROUND OF THE INVENTION

This invention relates to the use of at least one compound with a progesterone-antagonistic (PA) action for the production of pharmaceutical agents for the treatment of dysfunctional uterine bleeding.

Forms of dysfunctional uterine bleeding (dysfunctional or abnormal uterine bleeding, metrorrhagias and menorrhagias, hypermenorrhea) are forms of pathological bleeding that are not attributable to organic changes in the uterus (such as, e.g., endometrial carcinoma, myomas, polyps, etc.), systemic coagulation disorders, or a pathological pregnancy (e.g., ectopic pregnancy, impending abortion) (American College of Obstetricians and Gynecologists, 1982).

The average blood loss during normal menstruation is about 30 ml, whereby the period lasts for an average of 5 days. If the blood loss exceeds 80 ml, it is classified as pathological (Zahradnik HP, (1992) Menstruation. In Käser O et al. (editors) Gynäkologie und Geburtshilfe [Gynecology and Obstetrics], Vol. ½, Georg Thieme Verlag Stuttgart, New York: 7.31–7.51).

Metrorrhagias are defined as bleeding that may or may not be accompanied by pain and that cannot be linked to menstruation or cycle. If it lasts over 7 days, the blood loss often exceeds 80 ml.

Menorrhagia is menstruation that may or may not be accompanied by pain, normally every 27–28 days, which, when it lasts over 7 days, is associated in most cases with an increased blood loss of over 80 ml.

Hypermenorrhea is defined as menstruation that may or may not be accompanied by pain, normally every 27–28 days for 4–5 days with an elevated blood loss of over 80 ml.

Forms of dysfunctional uterine bleeding (mainly metrorrhagias and menorrhagias) are typical of adolescence and of the time of menopause, in which follicle-stimulating disorders, anovulation, and yellow-body and follicle persistence occur in clusters. The incidence of dysfunctional uterine bleeding is high and represents one of the most frequent reasons for gynecological consultation for women of reproductive age. The consultation rate because of dysfunctional uterine bleeding is 33% in reproductive age and 69% in perimenopause and postmenopause (Mencaglia, L., Perino, A., Hamon, J. (1987) Hysteroscopy in Perimenopausal and Postmenopausal Women with Abnormal Uterine Bleeding. J. Reprod. Med. 32:577).

The multiplicity of the treatments used with dysfunctional uterine bleeding is an indirect indication that the pathogenesis of this disease is still not clarified and no effective treatment yet exists. At this time, forms of dysfunctional uterine bleeding are treated with gestagens (e.g., 10 mg of medroxyprogesterone acetate daily, 0.7–1.0 mg of norethindrone acetate daily, each for 10–14 days), large-dose estrogen/gestagen combinations over a period of 10–14 days, but also with nonsteroidal cyclooxygenase inhibitors (e.g., mefenamic acid, naproxen, ibuprofen) and LHRH agonists (Cowan BD (1992) Dysfunctional Uterine Bleeding: Clues to Efficacious Approaches. In Alexander N.J., d'Arangues C (editors), Steroid Hormones and Uterine Bleeding, AAAS Press, 1922: 9–17).

The treatment with a large-dose estrogen/gestagen combination is associated with known cardiovascular risks (predominantly thromboembolic diseases). If treating dysfunctional uterine bleeding with medication is not successful, surgical methods (uterine curettage, hysterectomy) are recommended. After uterine myoma, dysfunctional uterine bleeding represents the second most frequent indication for this operation (Lee N C, Dicker R C, Rubin G L, Ory H W (1984) Confirmation of the Preoperative Diagnosis for Hysterectomy. Am. J. Obstet. Gynecol., 150: 283). It is noteworthy that it has not been possible in recent years to reduce the number of hysterectomies performed because of dysfunctional uterine bleeding, especially in the case of premenopausal women even though a wide variety of medicinal possibilities of treatment is available (Lumsden Mass., (1990) Menorrhagia—The Cost and Scope of Treatment. In Shaw RW (editor) Dysfunctional Uterine Bleeding. The Parthenon Publishing Group: 85–96). Hysterectomy carries risks that should not be underrated. The mortality rate after a hysterectomy is 6 per 100,000 (Wingo et al., 1985).

SUMMARY OF THE INVENTION

The object of the invention is therefore to provide a pharmaceutical agent for the indication provided, which halts dysfunctional bleeding and does not exhibit or exhibits only to a slight extent the undesirable effects of large-dose estrogen/gestagen preparations.

Such a new medicinal approach is the use of competitive progesterone antagonists (antigestagens) for the production of a pharmaceutical agent for the indication provided.

Antigestagens, if they are administered in the luteal phase, are able to induce menstruation-like bleeding (Nieman L K, Healy D L, Spitz I M, Nisula B C, Merriam G R, Bardin C W, Loriaux D L, Chrousos G P (1985) Use of Single Doses of the Antiprogesterone Steroid R U 486 for Induction of Menstruation in Normal Women. In Baulieu E E; Segal S J (editors): The Antiprogestin Steroid RU 486 and Human Fertility Control, Plenum Press, New York and London: 279–285). Experiments on primates show that antigestagen-induced bleeding leads to complete elimination of the endometrial tissue (Chilik C F, Hsiu J G, Acosta A A, van Uem JFHM, Hodgen G D (1986) RU 486-Induced Menses in Cynomolgus Monkeys: Uniformity of Endometrial Sloughing. Fertil Steril [Fertile Sterile] 45:708). The exact mechanism by which bleeding is induced by the drop in progesterone in a normal cycle or by antigestagen treatment has yet to be clarified. It is assumed that the progesterone deprivation leads to an induction of uterine prostaglandins, which induce bleeding (Zahradnik HP, (1992), loc. cit.).

It is also known that progesterone inhibits the synthesis of endothelin in the uterus and stimulates its enzymatic degradation (Casey M L, MacDonald PC (1992), Modulation of Endometrial Blood Flow: Regulation of Endothelin-1 Biosynthesis and Degradation in Human Endometrium. In Alexander N.J., d'Arcangues C (editors), Steroid Hormones and Uterine Bleeding. AAAS Press, 1992: 210224). Endothelin is regarded as the most potent vasoconstrictive endogenic substance. It is assumed that the increased release of endothelin at the end of a normal cycle results in constriction of spiral arterioles in the endometrium because of the drop in progesterone and as a result induces menstrual bleeding (Casey and MacDonald (1992), loc. cit.).

It has now been found, surprisingly enough, that competitive progesterone antagonists are able to produce a cessation of bleeding owing to vasoconstriction of endometrial arteries by the increase of uterus contractions and the thus-produced action on the myometrium, in the case of dysfunctional uterine bleeding. In the case of dysfunctional uterine bleeding, namely the activation of mechanisms that result in vasoconstriction of endometrial arteries appears to be inadequate because of a drop in progesterone that is incomplete or lasts too long.

Undesirable side effects, such as those that can occur in treatment with large-dose estrogen/gestagen preparations, are not observed when using competitive progesterone antagonists. The latter can be regarded as substances without significant side effects.

To date, nothing is known about the treatment of dysfunctional uterine bleeding with antigestagens in the normal cycle. Rather, attention is directed to the use of gestagens for this indication (Cowan 1992, loc. cit.). The fact that it is possible to reduce the occurrence of instances of breakthrough bleeding that happen when treatment is carried out with a low-dose estrogen- and gestagen-containing oral contraceptive owing to inadequate cycle control because of the low dosage is described in international patent application WO-A-93/17686. The use of progesterone-antagonistically active compounds by themselves or in combination with antiestrogenically active compounds for the production of pharmaceutical agents for inducing labor, for termination of pregnancy, and for treatment of gynecological disorders (dysmenorrhea, endometriosis) is already described in EP-A-0310541.

The pharmaceutical agents that are produced according to the invention are suitable for the treatment of all forms of dysfunctional uterine bleeding, such as menorrhagias, metrorrhagias, and hypermenorrhea.

As competitive PA, all compounds are suitable that themselves or whose metabolites block the action of progesterone on its receptor; for example, the following steroids:

11β-((4-N,N-Dimethylamino)-phenyl-17β-hydroxy-17α-propinyl-4,9(10)-estradien-3-one (RU-38486), 11β-((4-N,N-dimethylamino)-phenyl)-17β-hydroxy-18-methyl-17α-propinyl-4,9(10)-estradien-3one and 11β-((4-N,N-dimethylamino)-phenyl)-17aβ-hydroxy-17aα-propinyl-D-homo-4,9(10),16-estratien-3-one (all EP-A-0 057 115), also 11β-p-methoxyphenyl-17β-hydroxy-17α-ethinyl-4,9 (10)-estradien-3-one (Steroids 37 (1981), 361–382), 11β-(4-acetylphenyl)-17β-hydroxy-17α-(prop-1-inyl)-4, 9(10)-estradien-3-one (EP-A 0 190 759), as well as the 11β-aryl-14β-estradienes and -trienes that are described in EP-A 0 277 676, the 19,11β-bridged steroids that are the object of EP-A-0 283 428, the 11β-aryl-6-alkyl (or 6-alkenyl or 6-alkinyl)-estradienes and -pregnadienes that are known from EP-A-0 289 073 and the 11β-aryl-7-methyl (or 7-ethyl)-estradienes that are known from EP-A-0 321 010 as well as the 10β-H steroids of EP-A-0 404 283, for example, (Z)-11β-[4-(dimethylamino)phenyl]-17β-hydroxy-17α-(3-hydroxy-1-propenyl)-estr-4-en-3-one.

In addition, the following can be mentioned as typical representatives of competitive progesterone antagonists that are to be used according to the invention, for example:

11β-(4-Dimethylaminophenyl)-17α-hydroxy-17β-(3-hydroxypropyl)-13α-methyl-4,9-gonadien-3-one (EP-A-0 190 759);

11β,19-(4-acetylphenyl)-17β-hydroxy-17α-(3-hydroxyprop-1-(Z)-enyl)-4,9(10)-estradien-3-one (EP-A-0 190 759);

11β19-(4-(cyanophenyl)-17β-hydroxy-17α-(3-hydroxyprop-1(Z)-enyl)-4-androsten-3-one and 11β,19-(4-(3-pyridinyl)-o-phenylene)-17β-hydroxy-17α-(3-hydroxyprop-1-(Z)-enyl)-4-androsten-3-one (both WO-A-93/23020).

For treatment of dysfunctional uterine bleeding with PA, in general, according to the invention, short-term treatment (daily to 1 to at most 10 days) at a daily dose of 1 to 600 mg of the competitive progesterone antagonist per day is sufficient.

Preferably, according to the invention, an amount of 5 to 400 mg is administered daily. Especially preferred is the daily administration of 50 to 400 mg of 11β-(4-dimethylaminophenyl)- 17α-hydroxy-17β-(3-hydroxypropyl)-13α-methyl-4,9-gonadien-3-one (onapristone) or of 50 to 400 mg of (Z)-11β-[4-(dimethylamino)-phenyl]-17β-hydroxy-17α-(3-hydroxy-1-propenyl)-estr-4-en-3-one.

The one-time administration of a competitive progesterone antagonist within the indicated dosage range may be sufficient by itself to stop the bleeding, particularly when a dosage within the especially preferred dosage range of onapristone or (Z)-11β-[4-(dimethylamino)phenyl]-17β-hydroxy-17α-(3-hydroxy-1-propenyl)-estr-4-en-3-one is selected. Otherwise, treatment is continued until the bleeding stops, which in most cases occurs within 5 days at the latest.

According to the invention, both the acute treatment of associated dysfunctional uterine bleeding and the prophylactic prevention of such bleeding are possible.

The competitive progesterone antagonist can be administered, e.g., locally, enterally, or parenterally, for use according to the invention. For the preferred enteral administration, especially tablets, coated tablets, capsules, pills, suspensions, or solutions are suitable, which can be produced in the usual way with the additives and vehicles that are commonly used in galenicals. For local or topical use, for example, vaginal suppositories are suitable.

By way of example, the example below shows the formulation of a competitive progesterone antagonist for use according to the invention. Other progesterone antagonists can be formulated quite similarly, whereby each amount that is described above as suitable can be contained in the formulation.

EXAMPLES

Formulation Example 100.0 mg of 11β-[(4-N,N-dimethylamino)-phenyl]-17α-hydroxy-17b-(3-hydroxypropyl)-13α-methyl-4,9-gonadien-3-one 140.5 mg of lactose 69.5 mg of corn starch 2.5 mg of polyvinyl pyrrolidone 2.0 mg of aerosil 0.5 ma of magnesium stearate 315.0 mg of the total weight of the tablet, which is produced in the usual way on a tablet press.

Example 1

Acute Treatment of Metrorrhagias by One-time Administration of Onapristone

Women with dysfunctional metrorrhagias are orally treated on a one-time basis with 200–400 mg of onapristone. Preferred is treatment in the luteal phase of the cycle. The treatment results in a cessation of bleeding within 2–4 days.

Example 2
Acute Treatment of Menorrhagias and Hypermenorrhea by One-time Administration of Onapristone Women with menorrhagias and hypermenorrhea are orally treated on a one-time basis with 200–400 mg of onapristone on the 28th day of the cycle or on the first day of bleeding. The treatment induces menstruation-like bleeding of normal intensity (about 30 ml) and duration (about 5 days).

Example 3
Prophylactic Treatment of Metrorrhagias by One-time Administration of Onapristone Women with dysfunctional metrorrhagias are orally treated on a one-time basis with 200–400 mg of onapristone every 28 days. The treatment induces menstruation-like bleeding of normal intensity (about 30 ml) and duration (about 5 days) and prevents the occurrence of metrorrhagias. The treatment is continued for 3–6 cycles.

Example 4
Prophylactic Treatment of Menorrhagias and Hypermenorrhea by One-time Administration of Onapristone Women with menorrhagias and hypermenorrhea are orally treated with 200–400 mg of onapristone every 28 days. The treatment induces menstruation-like bleeding of normal intensity (about 30 ml) and duration (about 5 days) and prevents the occurrence of menorrhagias and hypermenorrhea. The treatment is continued for 3–6 cycles.

Example 5
Acute Treatment of Metrorrhagias by Repeated Administration of Onapristone Women with dysfunctional metrorrhagias are orally treated until bleeding ceases with 200–400 mg/day of onapristone, at most over 10 days. The beginning of treatment is to be preferably in the luteal phase of the cycle.

Example 6
Acute Treatment of Menorrhagias and Hypermenorrhea by Repeated Administration of Onapristone Women with menorrhagias and hypermenorrhea are orally treated until bleeding ceases on the 28th day of the cycle or on the first day of bleeding with 200–400 mg/day of onapristone, at most over 10 days. The treatment induces menstruation-like bleeding of normal intensity (about 30 ml) and duration (about 5 days) and thus prevents increased blood loss.

Example 7
Prophylactic Treatment of Metrorrhagias by Repeated Administration of Onapristone Women with dysfunctional metrorrhagias are orally treated every 28 days for a maximum of 10 days with 200–400 mg/day of onapristone. The treatment induces menstruation-like bleeding of normal intensity (about 30 ml) and duration (about 5 days) and prevents the occurrence of metrorrhagias. The treatment is continued over 3–6 cycles.

Example 8
Prophylactic Treatment of Menorrhagias and Hypermenorrhea by Repeated Administration of Onapristone Women with menorrhagias and hypermenorrhea are orally treated every 28 days for a maximum of 10 days with 200–400 mg/day of onapristone. The treatment induces menstruation-like bleeding of normal intensity (about 30 ml) and duration (about 5 days) and prevents the occurrence of menorrhagias and hypermenorrhea. The treatment is continued for 3–6 cycles.

In the case of the treatment of dysfunctional uterine bleeding according to the invention by using a competitive progesterone antagonist, both the otherwise observed bleeding duration is thus shortened and the intensity, i.e., the blood loss, is drastically reduced.

What is claimed is:

1. A method for the treatment of dysfunctional uterine bleeding, consisting essentially of administering a progesterone antagonist in an amount effective to treat dysfunctional uterine bleeding to a woman in need of said treatment.
2. The method according to claim 1, in which the dysfunctional uterine bleeding is a metrorrhagias.
3. The method according to claim 1, in which the dysfunctional uterine bleeding is a menorrhagia.
4. The method according to claim 1, in which the dysfunctional uterine bleeding is a hypermenorrhea.
5. The method according to claim 1, comprising administering $11\beta$-((4-N,N-Dimethylamino)-phenyl-$17\beta$-hydroxy-$17\alpha$-propinyl-4,9(10)-estradien-3-one-(RU-38486), $11\beta$-((4-N,N-dimethylamino)-phenyl)-$17\beta$-hydroxy-18-methyl-$17\alpha$-propinyl-4,9(10)-estradien-3-one, $11\beta$-((4-N,N-dimethylamino)-phenyl)-$17\alpha\beta$-hydroxy-$17a\alpha$-propinyl-D-homo-4,9(10),16-estratien-3-one, $11\beta$-p-methoxyphenyl-$17\beta$-hydroxy-$17\alpha$-ethinyl-4,9(10)-estradien-3-one, $11\beta$-(4-acetylphenyl)-$17\beta$-hydroxy-$17\alpha$-(prop-1-inyl)-4,9(10)estradien-3-one, $11\beta$-(4-dimethylaminophenyl)-$17\alpha$-hydroxy-$17\beta$-(3-hydroxy-propyl)-$13\alpha$-methyl-4,9-gonadien-3-one, (Z)-$11\beta$-[4-(dimethylamino)phenyl]-$17\beta$-hydroxy-$17\alpha$-(3-hydroxy-1-propenyl)-estr-4-en-3-one-5, $11\beta$, 19-(4-acetylphenyl)-$17\beta$-hydroxy-$17\alpha$-(3-hydroxyprop-1-(Z)-enyl)-4, 9(10)-estradien-3-one, $11\beta$, 19-(4-cyanophenyl)-$17\beta$-hydroxy-$17\alpha$-(3-hydroxyprop-1-(Z)-enyl)-4-androsten-3-one or $11\beta$, 19-(4-(3-pyridinyl)-o-phenylene)-$17\beta$-hydroxy-$17\alpha$-(3-hydroxyprop-1-(Z)-enyl)-4-androsten-3-one.

6. The method according to claim 1, comprising administering 1 to 600 mg of a progesterone antagonist in a daily dosage unit.
7. The method according to claim 6, comprising administering 50 to 400 mg of a progesterone antagonist.
8. The method according to claim 6, comprising administering 50 to 400 mg of $11\beta$-(4-dimethylaminophenyl)-$17\alpha$-hydroxy-$17\beta$-(3-hydroxy-propyl)-$13\alpha$-methyl-4,9-gonadien-3-one or 50 to 400 mg of (Z)-$11\beta$-[4-(dimethylamino)phenyl]-$17\beta$-hydroxy-$17\alpha$-(3-hydroxy-1-propenyl)-ester-4-en-3-one.

9. A method for the treatment of dysfunctional uterine bleeding which is metrorrhagia, menorrhagia or hypermenorrhea, consisting essentially of administering an effective amount of a progesterone antagonist to a woman in need of said treatment.
10. A method for the treatment of dysfunctional uterine bleeding, comprising administering a progesterone antagonist in an amount effective to treat dysfunctional uterine bleeding to a woman in need of said treatment, over a period of 1 to at most 10 days.
11. The method of claim 10, wherein the administration is a one-time administration.

* * * * *

UNITED STATES PATENT AND TRADEMARK OFFICE
CERTIFICATE OF CORRECTION

PATENT NO.   : 6,451,780 B1
DATED        : September 17, 2002
INVENTOR(S)  : Chwalsz et al.

It is certified that error appears in the above-identified patent and that said Letters Patent is hereby corrected as shown below:

<u>Column 6,</u>
Line 12, change "metrorrhagias" to -- metrorrhagia --.

Signed and Sealed this

Tenth Day of June, 2003

JAMES E. ROGAN
*Director of the United States Patent and Trademark Office*